United States Patent [19]
Buckberg et al.

[11] Patent Number: 5,643,191
[45] Date of Patent: Jul. 1, 1997

[54] CARDIOPLEGIA DELIVERY SYSTEM AND METHOD FOR CONVERTING FROM WARM CARDIOPLEGIA TO COLD CARDIOPLEGIA

[75] Inventors: Gerald D. Buckberg, Los Angeles; Russell A. Heimstaedt, Irvine; John M. Taylor, Trabuco Canyon, all of Calif.

[73] Assignee: Sorin Biomedical Inc., Irvine, Calif.

[21] Appl. No.: 381,690

[22] Filed: Jan. 26, 1995

[51] Int. Cl.$^6$ .............................. A61M 37/00; A61F 7/12
[52] U.S. Cl. ................................. 604/4; 604/113
[58] Field of Search .................... 604/4–6, 113, 604/118, 27–31, 65

[56] References Cited

U.S. PATENT DOCUMENTS

| | | |
|---|---|---|
| 3,825,060 | 7/1974 | Heller et al. |
| 4,065,264 | 12/1977 | Lewis. |
| 4,282,180 | 8/1981 | Raible. |
| 4,416,280 | 11/1983 | Carpenter et al. |
| 4,427,009 | 1/1984 | Wells et al. |
| 4,433,971 | 2/1984 | Lindsay et al. |
| 4,512,163 | 4/1985 | Wells et al. |
| 4,529,397 | 7/1985 | Hennemuth et al. .......... 604/4 |
| 4,559,999 | 12/1985 | Servas et al. |
| 4,568,330 | 2/1986 | Kajawski et al. |
| 4,653,577 | 3/1987 | Noda. |
| 4,883,455 | 11/1989 | Leonard ........................ 604/4 |
| 5,211,913 | 5/1993 | Hagiwara et al. ............. 604/4 |
| 5,255,734 | 10/1993 | Leonard et al. ............... 604/4 |
| 5,269,749 | 12/1993 | Koturov ........................ 604/4 |
| 5,322,500 | 6/1994 | Johnson et al. |
| 5,358,481 | 10/1994 | Todd et al. |
| 5,385,540 | 1/1995 | Abott et al. |
| 5,423,749 | 6/1995 | Merte et al. |

FOREIGN PATENT DOCUMENTS

PCT/US92/ 04028  5/1992  WIPO.

OTHER PUBLICATIONS

A Straight-Forward Approach To Cardioplegia Delivery (2 pages, 1985), Gish Biomedical, Inc.

All-Purpose Cardioplegia Heat Exchanger (5 pages, May 1987), Medtronic Electromedics.

CardioPlegia Over Pressure Valve, (1 page), American Omni Medical, Inc.

The Creation of a Classic. A Precision Engineered Cardioplegia Delivery System, (12 pages, May 1993), Bard Cardiopulmonary Division.

K$^+$ardia Cardioplegia Delivery System, (2 pages, 1993), Cobe Cardiovascular Inc.

New Approaches to Blood Cardopplegic Delivery to Reduce Hemodilution and Cardioplegic Overdose, Kai Ihnken, M.D., Kiyozo Morita, M.D., and Gerald D. Buckberg, M.D., J. Card. Surg., 1994;9:26–36.

Presenting the Sorin BCD Avanced. The Complete Picture of Consistent Performance. (2 pages), Sorin Biomedical, Inc.

Scimed's MYOtherm Cardioplegia System (2 pages).

Single Pass Blood Cardioplegia Systems (2 pages, Oct. 1992), Gish Biomedical, Inc.

With the Monolyth, Superior Performance is a Matter of Course. (10 pages), Sorin Biomedical, Inc.

*Primary Examiner*—John G. Weiss
*Assistant Examiner*—David J. Cho
*Attorney, Agent, or Firm*—Popovich & Wiles, P.A.

[57] ABSTRACT

A cardioplegia delivery system which includes a first delivery unit adapted for connection in a manner allowing delivery of cardioplegia fluid to a patient's heart during surgery. A second delivery unit may be added to the cardioplegia delivery system. The second delivery unit includes a heat exchanger for controlling the temperature of the cardioplegia fluid. The second delivery unit may be connected during the surgical procedure to allow conversion from warm cardioplegia delivery to cold cardioplegia.

6 Claims, 11 Drawing Sheets

CARDIOPLEGIA DELIVERY SYSTEM AND METHOD FOR CONVERTING FROM WARM CARDIOPLEGIA TO COLD CARDIOPLEGIA

Reference is made to our co-pending application, Ser. No. 08/379,393 filed on even date herewith entitled Apparatus And Method Of Cardioplegia Delivery which is hereby incorporated by reference.

FIELD OF THE INVENTION

This invention relates to apparatus and methods used in the administration of blood and cardioplegia solutions during cardiac surgery. More particularly, the invention is directed to a cardioplegia delivery device which may be used to deliver warm cardioplegia fluids and a method of converting to the delivery of cold cardioplegia fluids during the surgery.

BACKGROUND OF THE INVENTION

During open-heart surgery the blood of the patient is bypassed to an extracorporeal support system which supplies the pumping function of the heart and the oxygenation function of the lungs. This effectively isolates the heart enabling the surgeon to make the necessary repairs to the heart. During the surgery it is desirable to arrest the beating/pumping action of the heart. It is also important during the time that the heart is isolated from the blood supply circuit that the heart be protected from ischemia or lack of blood flow which can result in permanent damage to the heart.

It is well known that the heart may be protected during open heart surgery by utilizing a technique commonly known as cold cardioplegia. This involves administering to the heart a cooled cardioplegia fluid which may consist of a crystalloid chemical solution containing potassium and other additives or a mixture of the crystalloid solution with blood. Use of a cooled cardioplegia fluid comprising a mixture of oxygenated blood and crystalloid solution is known to be effective in keeping the heart arrested while at the same time keeping the heart oxygenated. The cardioplegia fluid is cooled by utilizing a cardioplegia delivery system which includes a heat exchanger.

In addition to the cold cardioplegia technique described above, some heart surgeons have more recently begun utilizing a technique called warm continuous blood cardioplegia. In this technique the cardioplegia fluid is not cooled and, consequently, it is not necessary to use a heat exchanger in the cardioplegia delivery system. This technique involves supplying a cardioplegia fluid mixture of warm oxygenated blood and cardioplegia solution throughout the cardiac surgery. This technique has gained acceptance among some surgeons as a safe and effective means of arresting and protecting the heart during surgery.

Whether warm cardioplegia or cold cardioplegia is prescribed by the physician, the manner of administration of the cardioplegia fluid during surgery is similar. Cardioplegia delivery systems include components which supply blood and cardioplegia solution, mix the desired ration of blood/cardioplegia solution and then supply the mixture to the patient's heart. A specific ratio of oxygenated blood with cardioplegia solution containing potassium and other additives, is delivered to the coronary arteries. The term cardioplegia fluid, as used herein, shall mean any ratio of blood to cardioplegia solution and shall include 100% blood or 100% cardioplegia solution. Once the heart is arrested, the delivery system continues to supply the cardioplegia fluid to keep the heart arrested and to deliver oxygen to the myocardium. Pressures and temperatures are monitored to avoid damage to the heart. At the end of the bypass procedure, 100% blood is commonly administered to flush the cardioplegia solution out of the myocardium allowing the heart to be returned to its normal sinus rhythm.

During the process of cardioplegia delivery several problems can arise. First, air bubbles can be created in the cardioplegia fluid. Second, if a line is clamped during the procedure the cardioplegia delivery system may become over pressurized. Thus, it would be highly desirable to provide a cardioplegia delivery device which is able to eliminate air bubbles which are inadvertently admitted into the cardioplegia fluid. It would also be advantageous to provide a cardioplegia delivery device which is able to safely and efficiently react to over pressurization of the system without damaging the components of the system or resulting in loss of losing the patient's blood or cardioplegia solution.

Further, when warm cardioplegia is indicated and prescribed by the physician it is desirable to use a cardioplegia delivery device which does not include a heat exchanger. This results both in a cost savings and in a reduction in priming volume. However, using present delivery devices it is difficult to reconnect the delivery circuit to include a heat exchanger during the course of the surgery if it becomes necessary to cool the heart with the cardioplegia fluid. Therefore, it would be desirable to provide a cardioplegia delivery system that can be used initially without a heat exchanger if warm cardioplegia is indicated and later be converted quickly and easily to include a heat exchanger if cold cardioplegia is indicated during the surgery.

SUMMARY OF THE INVENTION

In accordance with the present invention there is disclosed a cardioplegia delivery system for delivering cardioplegia fluid to the heart of a patient. The system includes a first delivery unit having a housing with cardioplegia fluid inlet and outlet ports. The cardioplegia outlet port is adapted for connection in a manner allowing delivery of the cardioplegia fluid to the patient. The delivery unit further includes an air removal element within the housing. The air removal element may include a membrane positioned at the top of the housing with a one-way valve located above the membrane. The membrane is adapted to allow air to pass through the membrane and to block the passage of fluids at normal operating pressures of the device. Air is allowed to escape through the one-way valve located at the top of the housing when the pressure reaches a predetermined air pressure based upon the design of the one-way valve. The air removal element may further include a screen positioned in the cardioplegia fluid flow path between the fluid inlet and fluid outlet.

The delivery system includes a second delivery unit having a housing defining a cardioplegia fluid flow path having cardioplegia fluid inlet and outlet ports at opposite ends of the flow path. The outlet port of the second delivery unit is connected to the inlet port of the first delivery unit. The second delivery unit may include an air removal element similar to that contained in the first delivery unit. The second delivery unit includes a heat exchange element positioned adjacent the cardioplegia fluid flow path which provides a means to control the temperature of the cardioplegia fluid. Either or both of the first and second delivery devices may also incorporate an integral pressure relief valve for diverting cardioplegia fluid should the pressure in the interior of the housing exceed a predetermined value based upon the design specifications of the pressure relief valve.

The invention may also comprise a method of converting the delivery of warm cardioplegia fluid to cold cardioplegia fluid during open heart surgery. The method comprises providing a first cardioplegia fluid delivery unit having a cardioplegia fluid inlet and a cardioplegia fluid outlet and further having an air elimination element. The method includes connecting the outlet of the first cardioplegia delivery unit to tubing in a manner that provides delivery of the cardioplegia fluid to the heart of the patient and connecting the cardioplegia inlet of the first cardioplegia delivery unit to a source of cardioplegia fluid which may comprise blood, a blood and cardioplegia solution mixture, or pure cardioplegia solution, or any combination thereof. The warm cardioplegia fluid is delivered to the patient for the duration of a first time period during which warm cardioplegia is indicated and prescribed by the physician. The method further includes disconnecting the cardioplegia fluid source from the cardioplegia fluid inlet of the first cardioplegia delivery unit after the duration of the first time period and providing a second cardioplegia fluid delivery unit having a cardioplegia fluid inlet and a cardioplegia fluid outlet. The second cardioplegia fluid delivery unit has an air elimination element and a heat exchanger for controlling the temperature of the cardioplegia fluid. The method includes reconnecting the cardioplegia fluid source to the input of the second delivery unit and connecting the output of the second delivery unit to the input of the first delivery unit and delivering a cooled cardioplegia fluid to the patient from the output of the first cardioplegia fluid delivery unit. Either the first delivery unit or the second delivery unit or both may include a pressure relief valve for diverting cardioplegia fluid from the delivery units should the interior pressure exceed a predetermined value which is dependent upon the design specifications of the pressure relief valve.

BRIEF DESCRIPTION OF THE DRAWINGS

The foregoing and other aspects of the present invention will be best appreciated with reference to the detailed description of the invention which follows when read in conjunction with the accompanying drawings wherein.

DETAILED DESCRIPTION OF THE INVENTION

The Cardioplegia System

Figure 1:
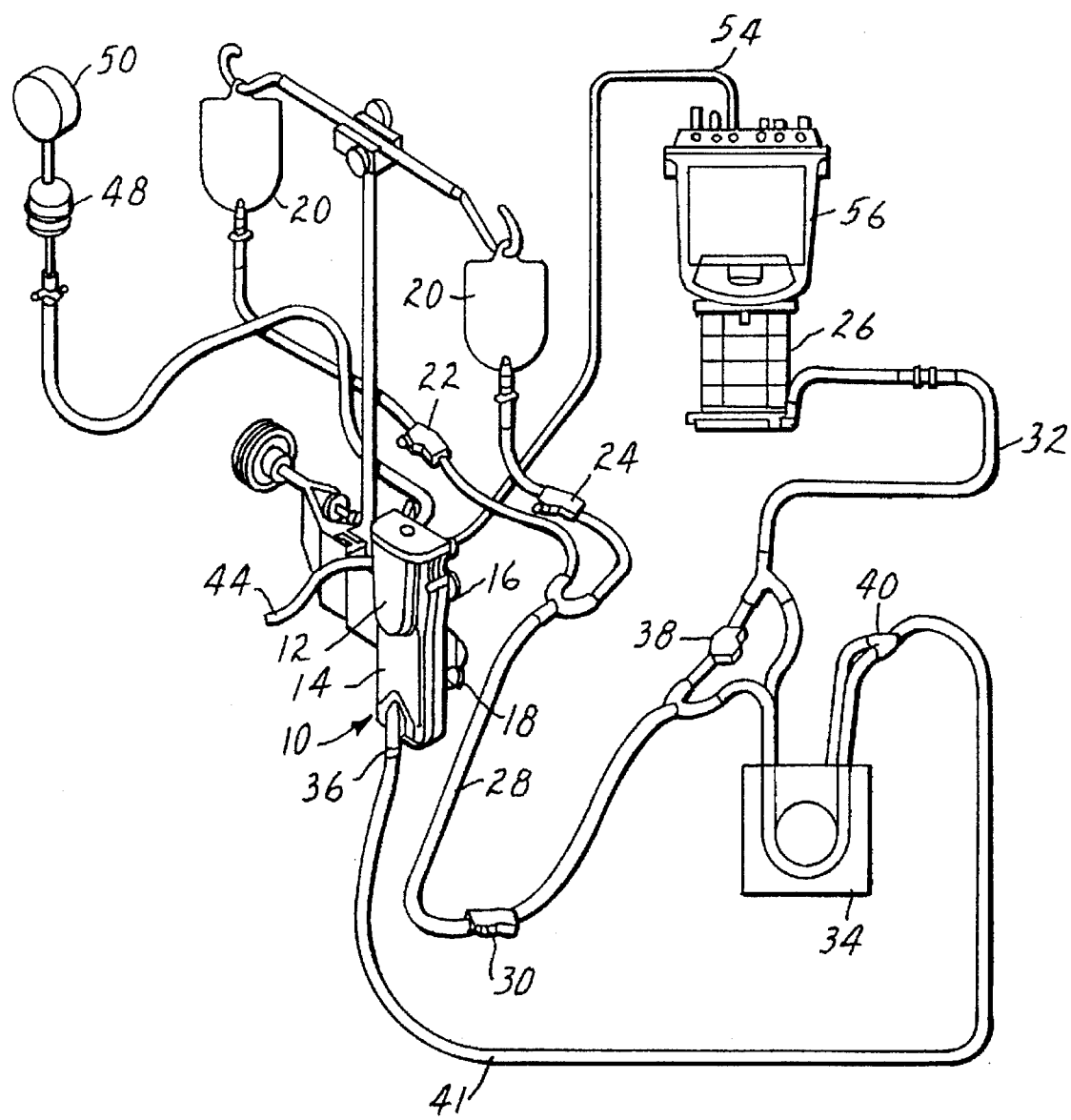
FIG. 1 is a schematic view of a cardioplegia delivery system which includes a cardioplegia delivery device in accordance with the present invention.
Figure 2:
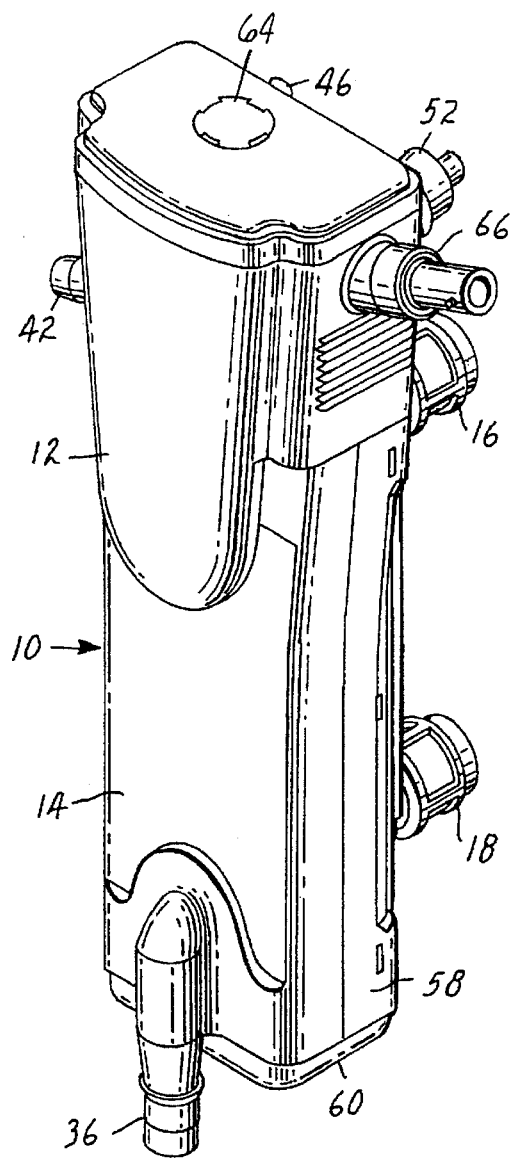
FIG. 2 is a perspective view of a cardioplegia delivery device with an integrated heat exchanger for use in cold cardioplegia delivery.

The cardioplegia delivery system of the present invention can be understood generally with reference to FIG. 1. The cardioplegia delivery system includes cardioplegia delivery device 10 which, in this embodiment includes an air chamber 12 and a heat exchanger 14. Cardioplegia delivery device 10 will be discussed in more detail with respect to FIGS. 2–7. In this embodiment heat exchanger 14 is incorporated with air chamber 12 into a single integral unit. Heat exchanger 14 and air chamber 12 may be bonded or affixed together in any conventional manner resulting in a fluid tight seal. Heat exchanger 14 includes an inlet 16 and an outlet 18 which, in operation, are connected to a source of heat exchange fluids (not shown) such as cold water. Although the embodiment of the cardioplegia delivery device 10 illustrated in FIG. 1 includes heat exchanger 14 the system shown may also be used with the cardioplegia delivery device shown in FIGS. 8–10 which is used for warm cardioplegia and does not include a heat exchanger.

The cardioplegia delivery system of FIG. 1 includes at least one cardioplegia solution source 20. In the embodiment disclosed two cardioplegia solution sources 20 are used. The sources may contain identical cardioplegia solution or one source may contain a cardioplegia solution having a higher concentration of potassium than the other. The higher concentration may be used initially with the lower concentration source being used after the heart has been arrested. The perfusionist may allow cardioplegia solution to flow through solution line 28 by opening shunt 30. Oxygenator 26 provides a source of oxygenated blood which is pumped through blood line 32 by roller pump 34 to the inlet 36 of cardioplegia delivery device 10. The delivery circuit may be provided with a shunt 38 which allows the perfusionist to supply pure blood to the cardioplegia delivery device 10.

Figure 4:
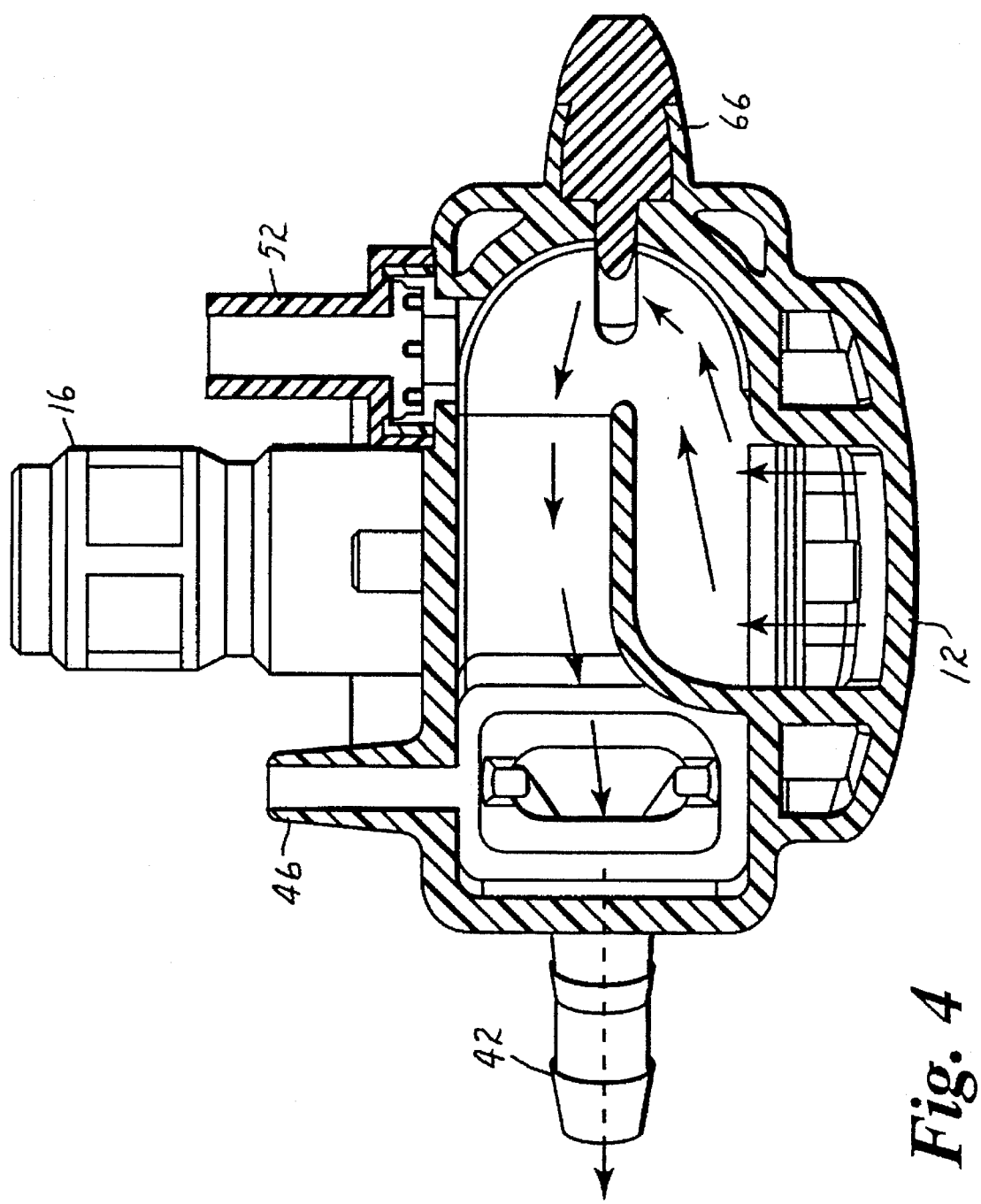
FIG. 4 is a top view in cross-section of the cardioplegia delivery device of FIG. 2 illustrating the cardioplegia fluid flow path.

Depending upon the size of the tubing and the activation of the various shunts in the delivery circuit the perfusionist is able to supply cardioplegia fluid to the inlet 36 of delivery device 10 in varying mixtures. It will be apparent that as the cardioplegia solution and blood are pumped through pump 34 they are mixed at a Y connection 40 prior to entering inlet 36 through cardioplegia fluid line 41. The cardioplegia fluid passes through heat exchanger 14 and air chamber 12 and exits the device through an outlet port 42 as better seen in FIG. 2. Outlet port 42 is connected to a patient return line 44 through which the cardioplegia fluid is delivered for perfusion of the patient's heart. Air chamber 12 includes a pressure monitor port 46 (as best seen in FIG. 4) which may be connected to a pressure transducer 48 for display of the internal pressure of the air chamber at pressure gauge 50.

Air chamber 12 also includes a pressure relief valve 52 as best seen in FIGS. 3–6. Pressure relief valve 52 is connected by tubing 54 to a cardiotomy reservoir 56. As will be discussed in more detail hereafter this allows cardioplegia fluid to be recirculated back to the cardiotomy reservoir if the internal pressure of the system exceeds a predetermined level.

Cold Cardioplegia Delivery Device

Figure 3:
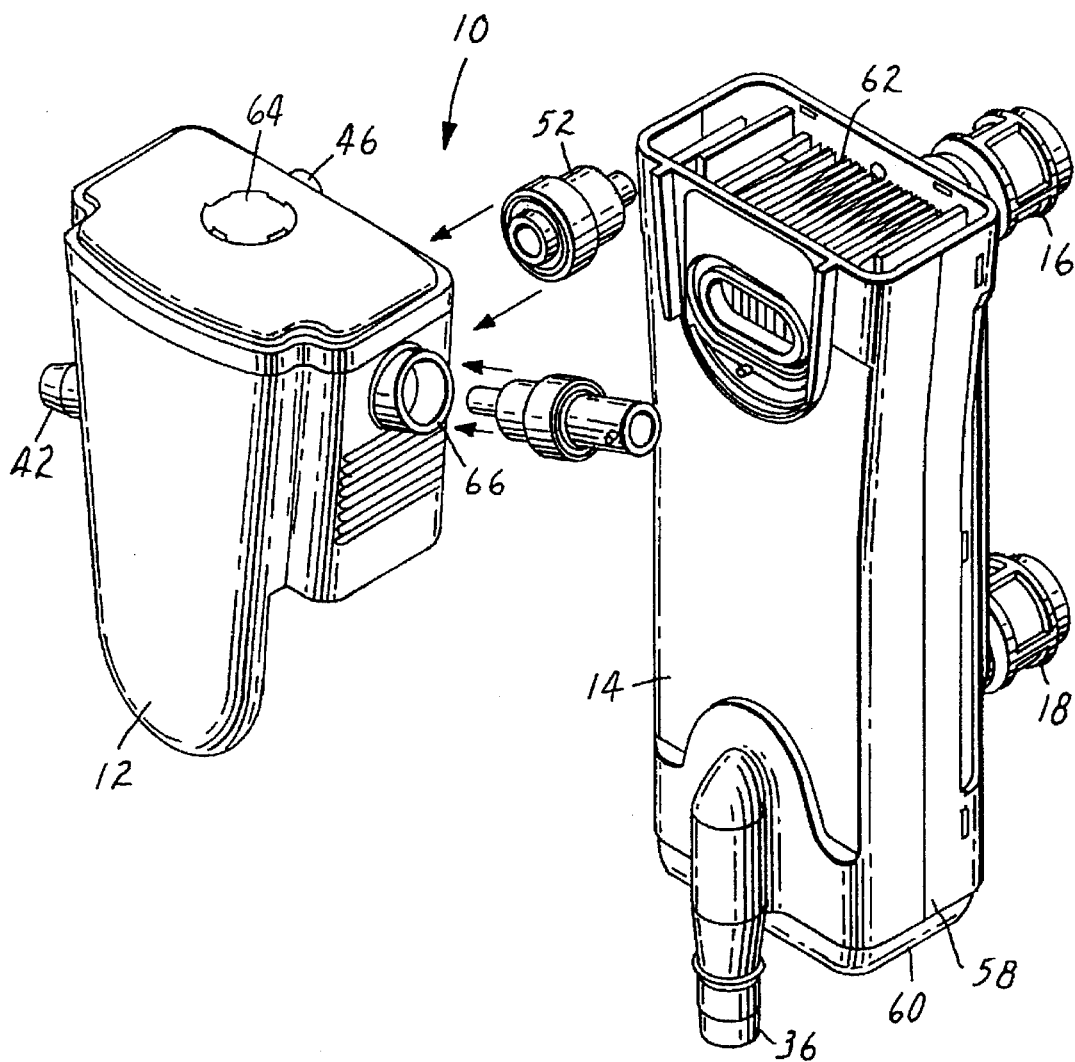
FIG. 3 is an exploded view of the cardioplegia delivery device of FIG. 2.

The cold cardioplegia delivery device 10 shown in FIG. 1 is set forth in more detail in FIGS. 2–7. As best seen in FIG. 3 device 10 comprises two distinct components, air chamber 12 and heat exchanger 14. Heat exchanger 14 includes a heat exchanger housing 58 and an end cap 60. A pleated heat exchange element 62 is contained within housing 58. Element 62 is comprised of a chevron-grooved, closely packed, pleated stainless steel sheet bent in an accordion fashion to create separate vertical channels. Cardioplegia fluid flows through the channels on one side of the stainless steel sheet while heat exchange fluid, typically water, is pumped into the unit through inlet 16, through the channels on the other side of heat exchange element 62 and out of the heat exchanger through outlet 18. By controlling the temperature of the water, one is able to control (heat or cool) the temperature of the cardioplegia fluid. The finned arrangement of the heat exchanger is designed to channel blood into a thin film for gentle mixing and efficient heat exchange yet allowing for ease of priming the unit without trapping air.

Figure 7:
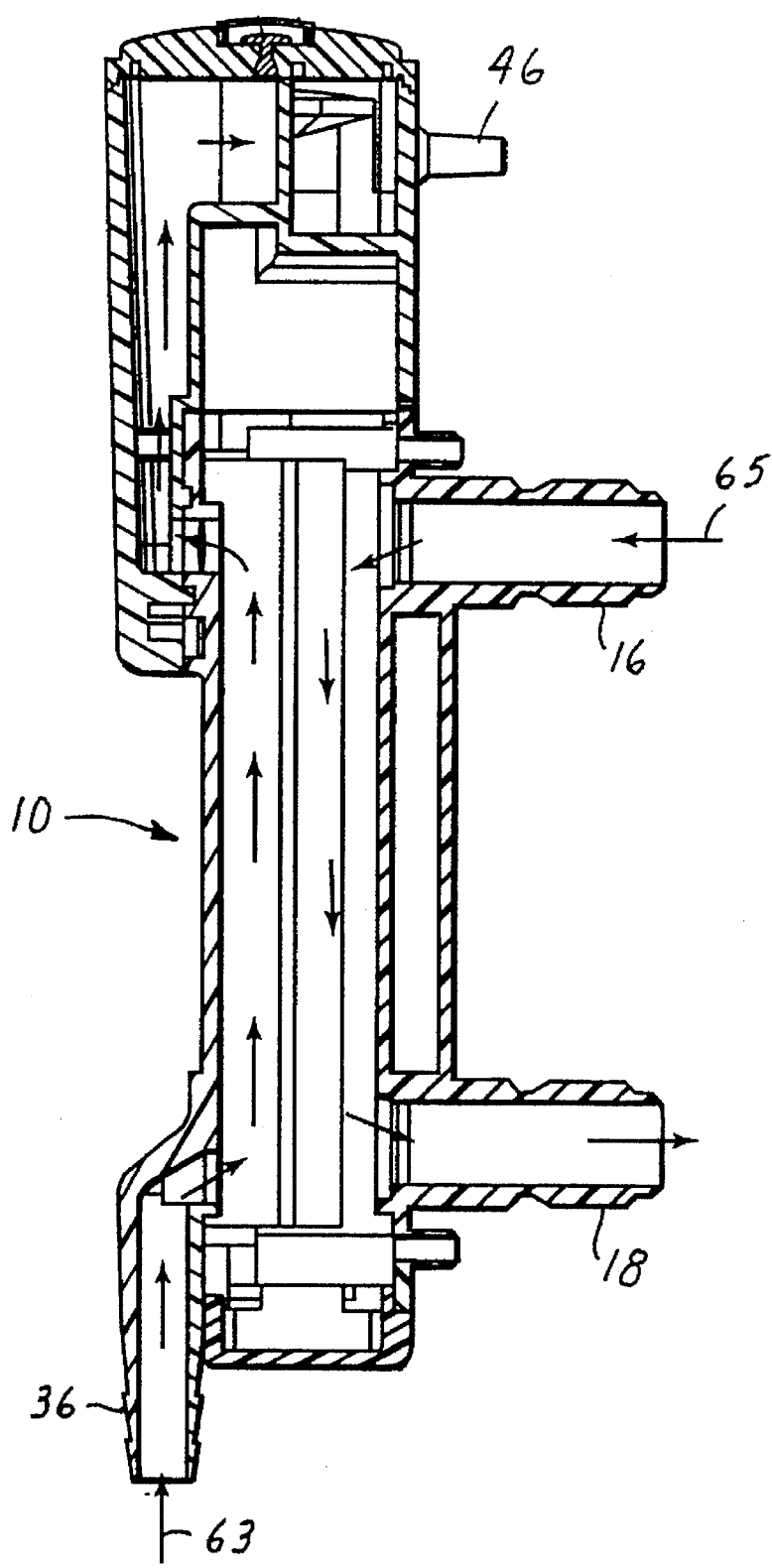
FIG. 7 is a cross-sectional side view of the cardioplegia delivery device of FIG. 2 showing the flow paths of the cardioplegia fluid and heat exchange fluid.

The flow paths of cardioplegia fluid (arrows 63) and water (arrows 65) through the heat exchanger are illustrated in FIG. 7. The flow paths are counter current thus providing for greater heat exchange efficiency. The flow paths on either side of the pleated fins are bounded at the top and bottom by potting material. The unit is constructed so that the fins extend through the potting material on both the top and bottom of the unit reducing the possibility of a water to cardioplegia fluid leak. Any fluid leaking through the potting material will leak to the atmosphere instead of the other side of the fin.

Figure 5:
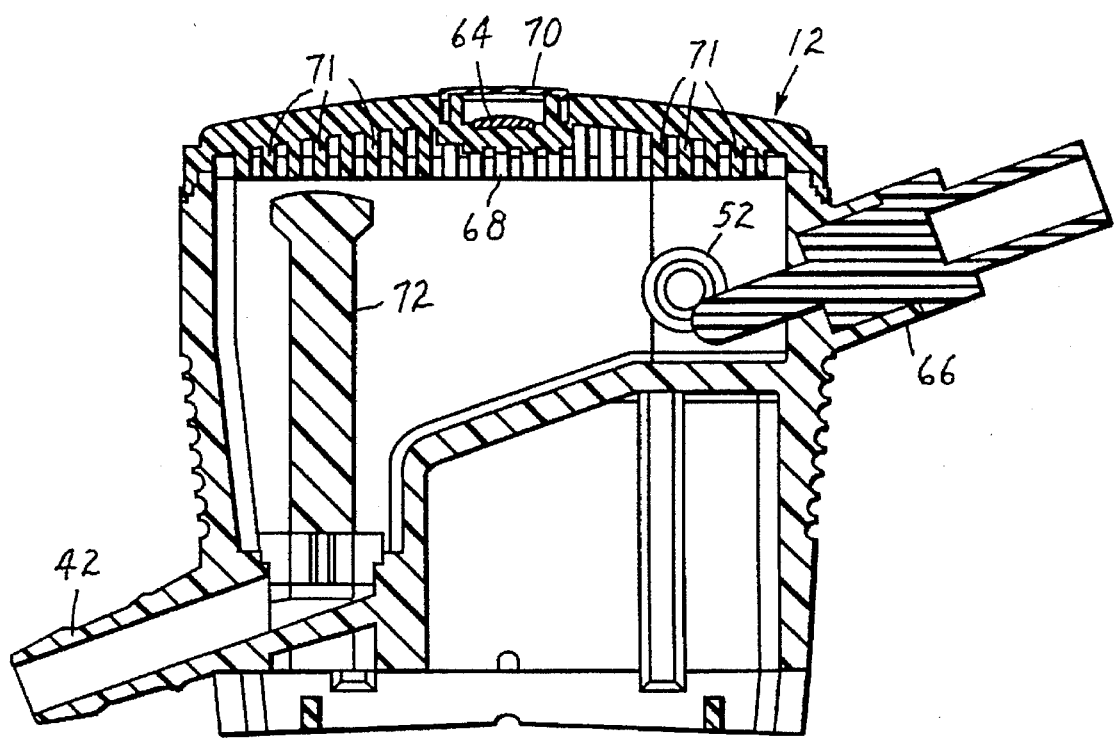
FIG. 5 is a cross-sectional view of the air chamber portion of the cardioplegia delivery device of FIG. 3.

Air chamber 12 includes a one-way air elimination valve 64 and a temperature port 66 as best seen in FIG. 5. Air chamber 12 includes a membrane 68 positioned at the top of the air chamber. In the preferred embodiment membrane 68 is comprised of a hydrophobic PTFE material with a pore size of 0.45 microns, a thickness of 0.01 cm and a surface area of 4.1 $cm^2$. Such a membrane will pass air but not fluids up to a pressure of 1300 mmHg. This is known as the water entry pressure of the membrane. Membrane 68 is supported by a plurality of support struts 71 which hold the membrane in place and prevent the shape of the membrane from distorting under pressure. Valve 64 prevents air from flowing back across the membrane into the cardioplegia fluid path in the event a negative pressure were created inside the air chamber. Valve 64 is a one-way umbrella check valve. In the preferred embodiment, valve 64 is comprised of silicone rubber and will release internal air pressure when it reaches 5 mmHg. The valve reseals when the internal pressure falls below 3 mmHg thus preventing outside air from flowing back into the air chamber. The one-way valve 64 is protected on top of the device with a vented plastic cover 70.

To further enhance the air elimination capacity of air chamber 12 a bubble screen 72 is included. Screen 72 is positioned in the cardioplegia fluid flow path just above the cardioplegia fluid outlet 42. Screen 72 serves two useful purposes. First, it deflects air bubbles in the cardioplegia fluid to the top of the air chamber where they can be eliminated across membrane 68. Second, the screen functions as a filter to remove solid particulate from the cardioplegia fluid before it is delivered to the patient's heart. In the preferred embodiment the screen is comprised of a 105 micron polyester mesh molded into a support structure of ABS plastic.

Figure 6:
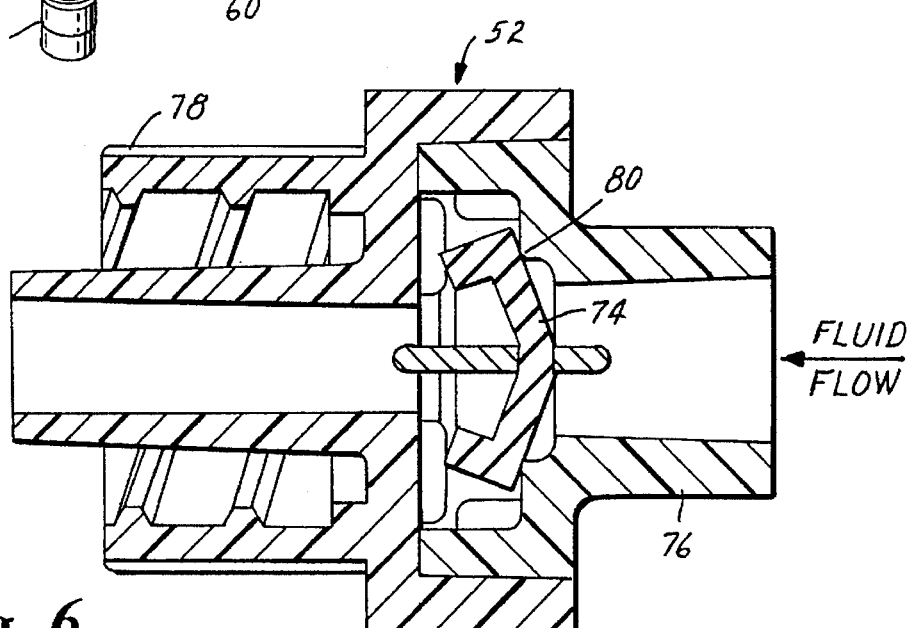
FIG. 6 is a cross-sectional view of the pressure relief valve utilized in the present invention.

Potential over pressurization of the device is prevented by pressure relief valve 52 which is mounted in the upper portion of air chamber 12. The specific construction of pressure relief valve is illustrated in FIG. 6. Valve 52 can be seen to comprise a molded disk cup 74 held between back housing 76 and front housing 78. Back housing 76 is securely fixed as by bonding or by other suitable means to air chamber 12 so that valve 52 is held securely in place. Under normal operating conditions disk 74 rests against disk seat 80 preventing the flow of fluid from the air chamber. However, the pressure relief valve 52 is designed to open to relieve internal pressure when the internal pressure reaches 600 mmHg or greater. When the pressure in the air chamber exceeds 600 mmHg the valve opens to divert fluid until the internal pressure falls to below 600 mmHg, at which time the molded disk cup 74 reseats and stops the flow of fluid. Pressure relief valve 52 eliminates the potential of rupturing the device or other circuit components or of reaching the water entry pressure of membrane 68. It should be appreciated that although a specific configuration has been illustrated for valve 52 other known valve configurations could be utilized within the scope of the present invention. Additionally, it is possible to select valves or valve material which will cause the valve to open at different internal pressures depending on the specific design criteria used.

Warm Cardioplegia

Figure 8:
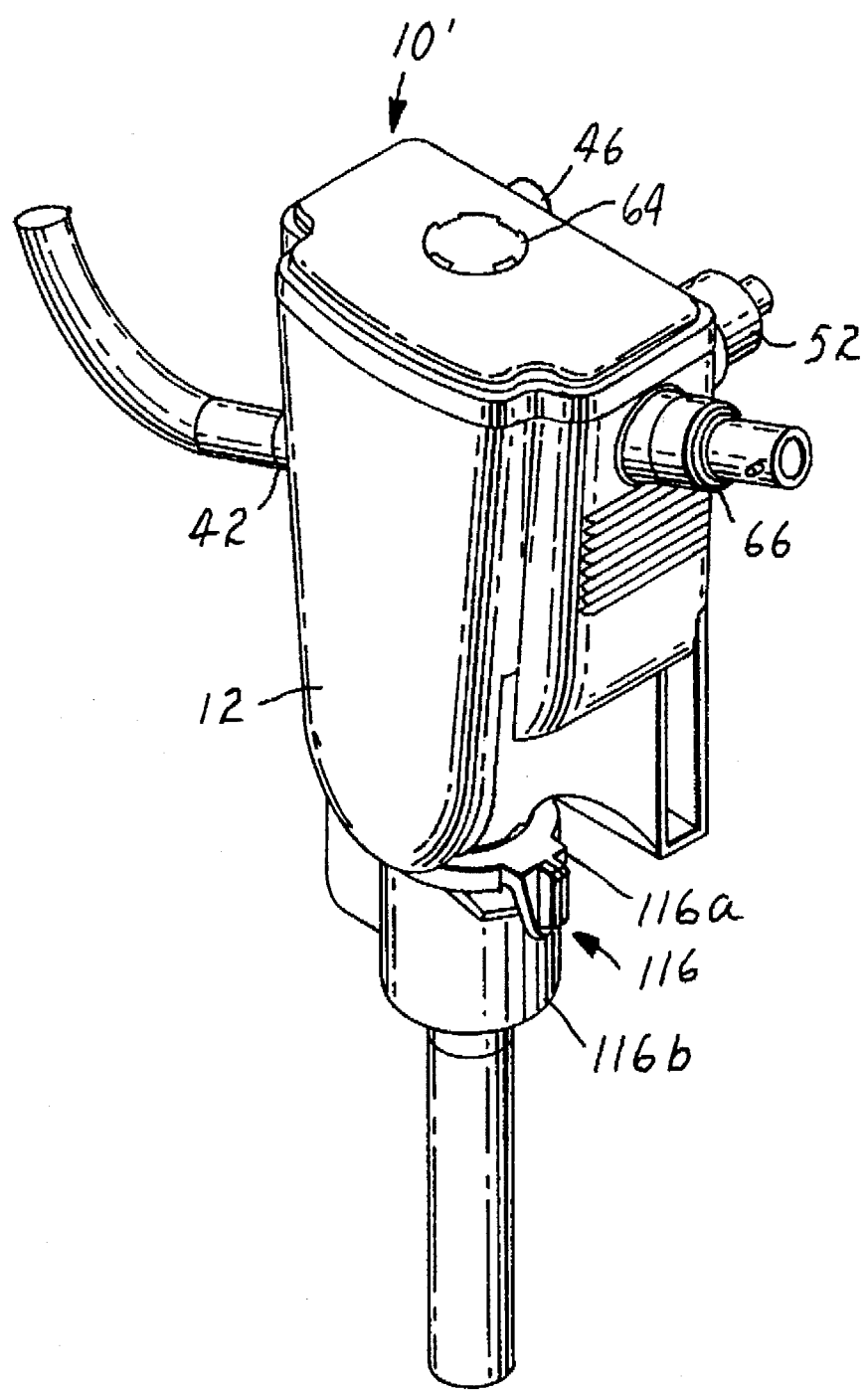
FIG. 8 is a perspective view of a cardioplegia delivery device utilized in the administration of warm cardioplegia.
Figure 9:
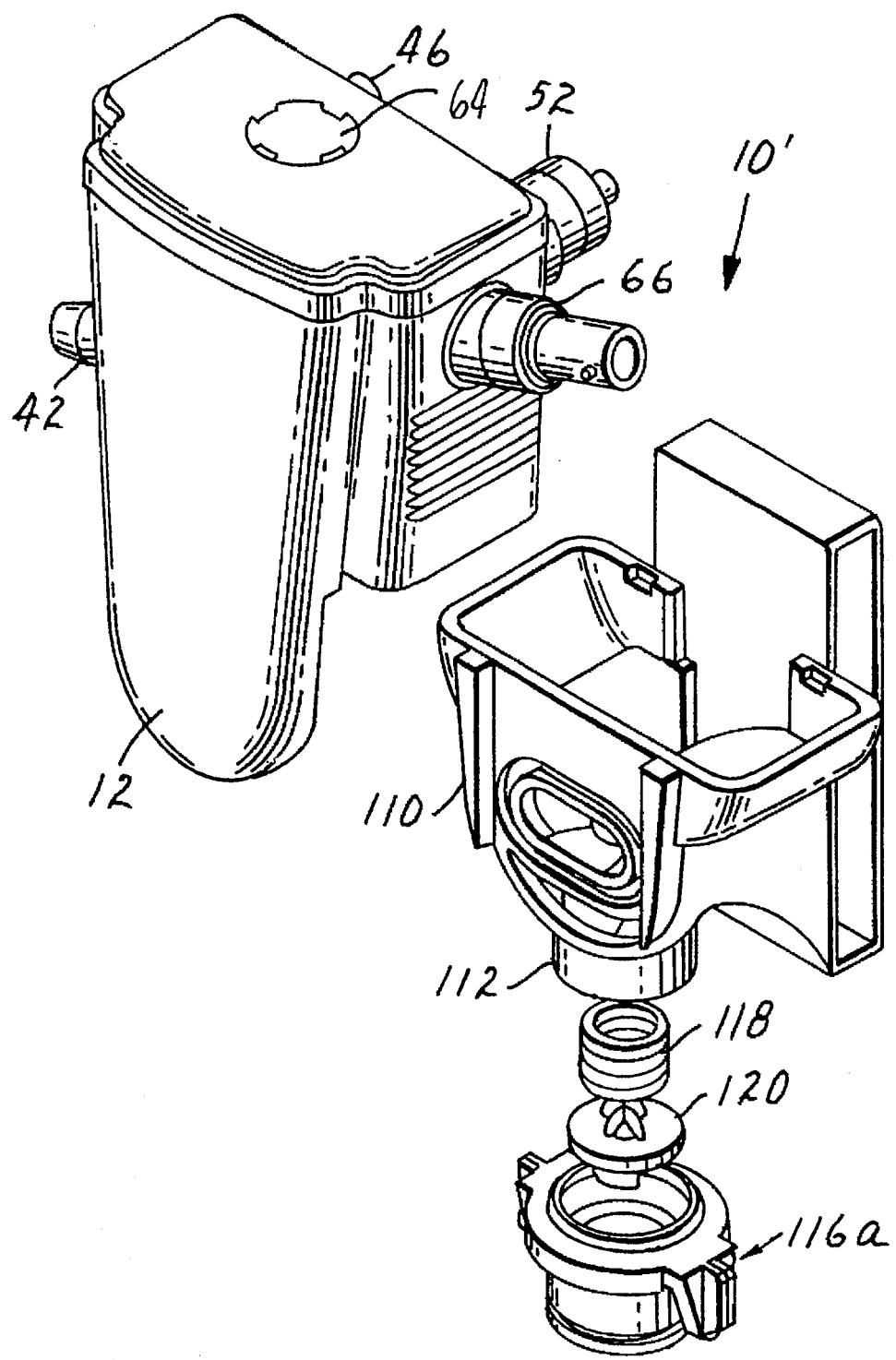
FIG. 9 is an exploded view of the cardioplegia delivery device of FIG. 8.
Figure 10A:
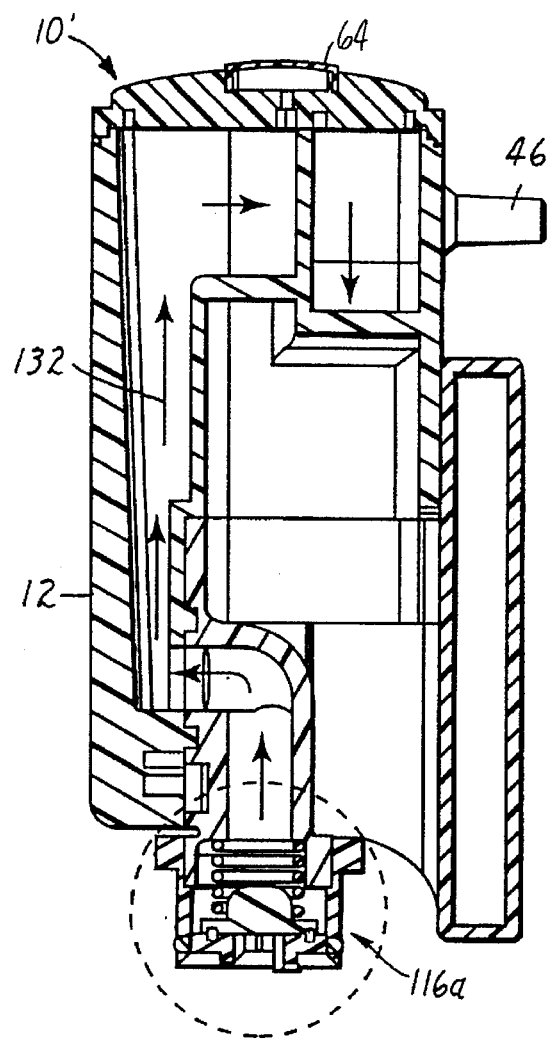
FIG. 10a is a cross-sectional side view of the cardioplegia delivery device of FIG. 8 illustrating the flow path of cardioplegia fluid and FIG. 10b is a magnified view in cross-section of the inlet of the delivery device.
Figure 10B:
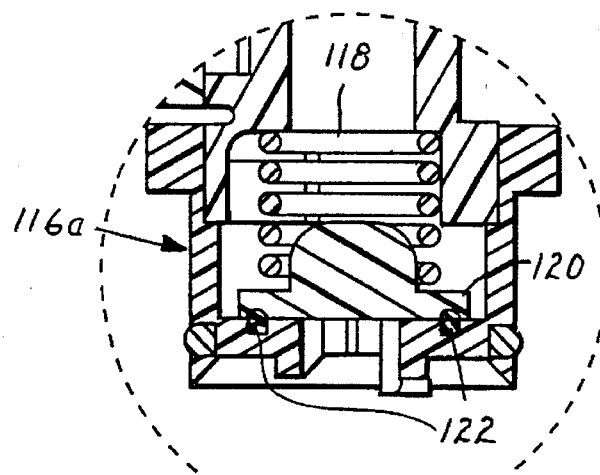

As previously mentioned, the cardioplegia delivery device 10 shown in FIG. 1 may include a heat exchanger (as shown) for cold cardioplegia delivery or it may consist of a device having no heat exchanger when warm cardioplegia is desired. Such a warm cardioplegia delivery device is shown in FIGS. 8–10. Cardioplegia delivery device 10' utilizes an air chamber which is identical to that utilized in the cold cardioplegia device described previously and, for purposes of clarity, like reference numerals will be used to identify the air chamber of the warm cardioplegia delivery device and its components.

As shown in FIG. 9 warm cardioplegia delivery device 10' is comprised of air chamber 12 which is securely bonded to a warm unit adapter 110. Warm unit adapter 110 includes an inlet into which the upper portion 116a of a valved connector 116 is attached. Upper portion 116a includes a spring 118 and a shut off valve 120. As best seen in FIG. 10a, when the upper portion 116a of connector 116 is not locked into position with the lower portion 116b, the base of shut off valve 120 is seated against O-ring 122 which blocks the flow of fluids through the connector.

Warm cardioplegia delivery device 10' is used when warm cardioplegia is desired. The method of use is identical to that described in connection with FIG. 1 except that no heat exchanger is provided to either cool or heat the cardioplegia fluid. The flow of cardioplegia fluid through warm cardioplegia delivery device 10' is shown in FIG. 10 by arrows 132.

Conversion from Warm Cardioplegia to Cold Cardioplegia During Surgery

Figure 11:
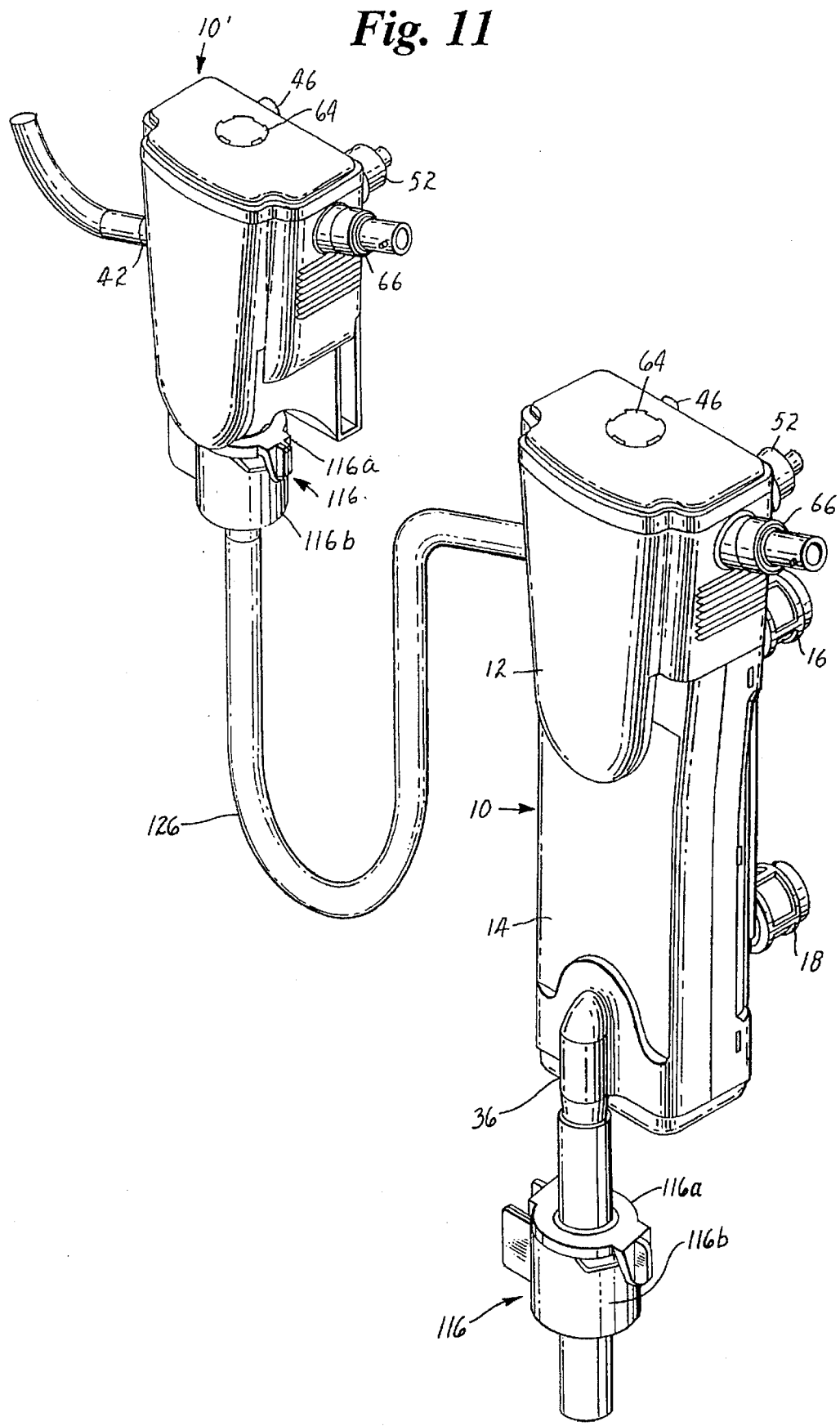
FIG. 11 is a schematic view of a cardioplegia delivery device utilized after the conversion from warm cardioplegia to cold cardioplegia delivery.

Although cold cardioplegia device 10 may be used to deliver warm cardioplegia if the heat exchanger is not used there are certain disadvantages to doing so. First, the price of device 10 is higher because of the inclusion of the heat exchanger. Second, the heat exchanger increases the priming volume of the unit. These disadvantages may be overcome by utilizing the warm cardioplegia delivery device disclosed in the present invention if warm cardioplegia is prescribed. By using this device it is possible during bypass surgery to convert from warm cardioplegia delivery to cold cardioplegia if the physician determines it is advisable to cool the heart. The conversion is accomplished by connecting cardioplegia device 10' in series with cardioplegia device 10 as shown in FIG. 11.

If warm cardioplegia is prescribed a delivery circuit such as that shown in FIG. 1 is used and cardioplegia delivery device 10' is used in place of delivery device 10. If at some point during the bypass surgery temperature control becomes necessary delivery device 10 with heat exchanger 14 incorporated therein may be connected in the circuit in series with device 10' in the manner depicted in FIG. 11.

Figure 12:
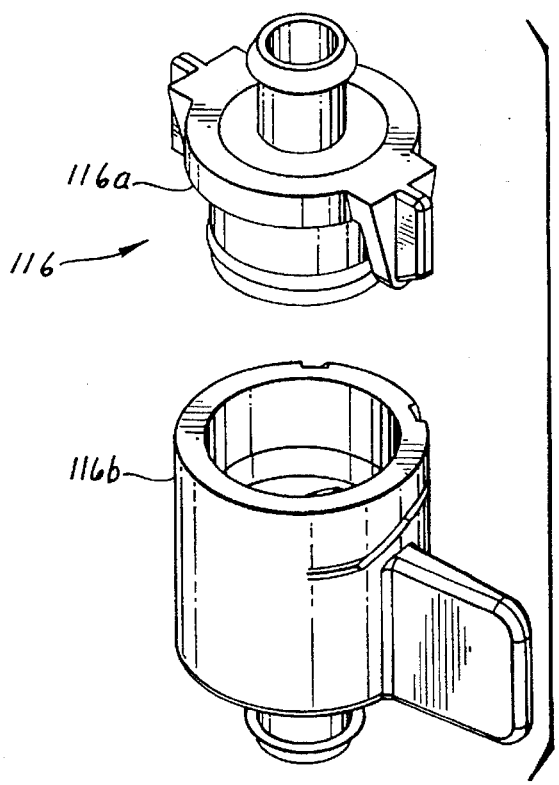
FIG. 12 is an exploded perspective view of the multi-position disconnect valve used in the present invention.
Figure 13:
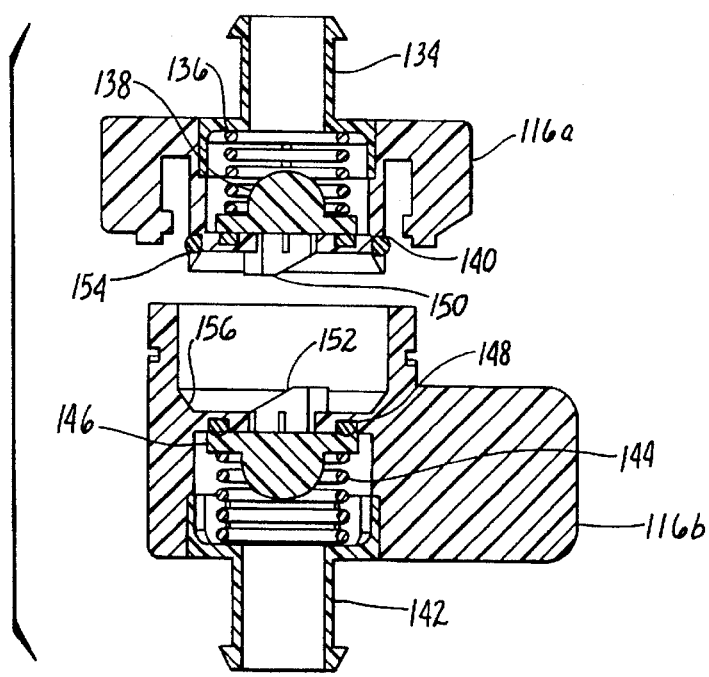
FIG. 13 is a side cross-sectional view of the valve of FIG. 12.

Cardioplegia device 10' is provided with multi-position valved disconnect 116. A valved disconnect 116 suitable for use in this invention is shown in detail in FIGS. 12 and 13. It should be understood that the upper portion 116a of the disconnect which is shown fitted at the inlet of warm unit adapter 110 has been modified to allow its attachment as shown in FIGS. 9 and 10. Valved disconnect 116 allows the operator to quickly disconnect the fluid line without discharging fluid. Disconnect 116 includes mated upper portion 116a and lower portion 116b. Upper portion 116a includes a connector stem 134 against which is seated a spring 136. Spring 136 biases a shut off valve 138 against an O-ring seal 140 to block the flow of fluids when the upper and lower portion of the valve are not in their final locked positions. Similarly, lower portion 116b has a connector stem 142, spring 144, shut off valve 146 and O-ring seal 148 which perform the same function. The upper and lower portions are mated together by twist locking them into place. The locking mechanism has two positions. The first locks the portions together but does not open shut off valves 138 and 146 to allow fluid flow. The second, locked, position is reached by further twisting the portions. This results in sections 150 and 152 being engaged with each other causing shut off valves 138 and 146 to be moved away from O-Ring seals 140 and 148, respectively. This opens the fluid flow in both portions of the valve. In the locked position O-ring 154 is seated on lip 156 preventing the valve from leaking. Device 10 is provided with tubing 126 extending from its outlet to the lower portion 116b of a valved disconnect 116. The inlet 36 of device 10 is connected to the upper portion 116a of a valved disconnect 116.

In use during the surgery the conversion from warm cardioplegia to cold cardioplegia may be made quickly and without spillage of cardioplegia fluid. It is anticipated that warm cardioplegia unit 10' will be supplied with a tubing pack which includes a multi-position valved disconnect 116 at its inlet. The cold cardioplegia unit will be supplied both as a stand alone unit meant for use if cold cardioplegia is desired or as an add on unit meant to be used to convert warm cardioplegia to cold cardioplegia. The add on unit shown in FIG. 11 will be supplied with a tubing pack which includes outlet tubing connected to the lower portion 116b of a disconnect valve 116 and inlet tubing connected to an upper portion 116a of a disconnect valve 116. Therefore, if during use of a warm unit 10' it is determined that cold cardioplegia is desirable the perfusionist need only disconnect the valve 116 at the inlet of unit 10' which closes the fluid flow valves in both the upper and lower portions of the valve. The add on unit is then inserted into the circuit by connecting the mating valve portions supplied with the add on unit to the upper and lower valve portions of the valve which has been disconnected. Once the connection is completed the flow of cardioplegia fluid is resumed.

Since cardioplegia devices 10 and 10' are both provided with similar air elimination mechanisms it is not necessary to prime the circuit before continued use. The membrane and one-way valve combinations in both devices will purge the units of air and prevent any air from being pumped to the patient.

From the foregoing detailed description of specific embodiments of the invention, it should be apparent that an improved cardioplegia delivery device has been disclosed. Although particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. For instance, the choice of materials or variations in the shape of the air chamber, heat exchanger or the components thereof or the substitution of disconnect valves of different configuration are believed to be a matter of routine for a person of ordinary skill in the art with knowledge of the embodiments disclosed herein.

We claim:

1. A cardioplegia delivery system for delivering cardioplegia fluid including blood, a blood and cardioplegia solution mixture, or cardioplegia solution, the system comprising:

a first delivery unit having a housing with cardioplegia fluid inlet and outlet ports, the cardioplegia fluid outlet port being adapted for connection in a manner allowing delivery of the cardioplegia fluid to a patient, the delivery unit further having an air removal element within the housing;

a second delivery unit having a housing defining a cardioplegia fluid flow path having cardioplegia fluid inlet and outlet ports at opposite ends thereof, the second delivery unit further having an air removal element within the housing and a heat exchange element adjacent the cardioplegia fluid flow path; and a disconnect valve having first and second detachable portions, the first portion having a shut-off valve configured to block the flow of cardioplegia fluid through the first portion when the first portion is detached from the second portion the first portion being connected to the inlet of the first delivery unit, the second portion being connected to the outlet of the second delivery unit.

2. The cardioplegia delivery system of claim 1 wherein the first delivery unit further comprises a pressure relief valve.

3. The cardioplegia delivery system of claim 1 wherein the second delivery unit further comprises a pressure relief valve.

4. The cardioplegia delivery system of claim 2 wherein the air removal element further comprises a screen positioned between the fluid inlet and the fluid outlet.

5. The cardioplegia delivery system of claim 1 wherein the heat exchange element is connected to the housing of the second delivery unit to form an integral structure.

6. The cardioplegia delivery unit of claim 1 wherein the second portion includes a shut-off valve configured to block the flow of cardioplegia fluid through the second portion when the second portion is detached from the first portion.

* * * * *